United States Patent [19]
Jalett et al.

[11] Patent Number: 5,886,225
[45] Date of Patent: Mar. 23, 1999

[54] PROCESS FOR THE HYDROGENATION OF IMINES

[75] Inventors: Hans-Peter Jalett, Dornach; Felix Spindler, Starrkirch-Wil; Reinhard Georg Hanreich, Basel, all of Switzerland

[73] Assignee: Novartis Crop Protection, Greensboro, N.C.

[21] Appl. No.: 973,575

[22] PCT Filed: Jun. 4, 1996

[86] PCT No.: PCT/EP96/02419

§ 371 Date: Dec. 5, 1997

§ 102(e) Date: Dec. 5, 1997

[87] PCT Pub. No.: WO96/41793

PCT Pub. Date: Dec. 27, 1996

[30] Foreign Application Priority Data

Jun. 8, 1995 [CH] Switzerland ............................ 1685/95

[51] Int. Cl.$^6$ .................................................. C07C 209/38
[52] U.S. Cl. ............................................................ 564/415
[58] Field of Search ............................................. 564/415

[56] References Cited

U.S. PATENT DOCUMENTS

| 4,994,615 | 2/1991 | Spindler et al. . |
| 5,011,995 | 4/1991 | Pugin et al. . |
| 5,112,999 | 5/1992 | Osborn et al. . |
| 5,463,097 | 10/1995 | Togni et al. . |

FOREIGN PATENT DOCUMENTS

| 256982 | 2/1988 | European Pat. Off. . |
| 301457 | 2/1989 | European Pat. Off. . |
| 564406 | 10/1993 | European Pat. Off. . |
| WO 95/21176 | 8/1995 | WIPO . |

OTHER PUBLICATIONS

Angewandte Chemie, International Edition, vol. 29, No. 5, pp. 558–559, May 1990.

*Primary Examiner*—Brian M. Burn
*Attorney, Agent, or Firm*—William A. Teoli, Jr.

[57] ABSTRACT

A process for the hydrogenation of imines with hydrogen under elevated pressure in the presence of iridium catalysts and with or without an inert solvent, wherein the reaction mixture contains hydrogen iodide.

41 Claims, No Drawings

PROCESS FOR THE HYDROGENATION OF IMINES

The present invention relates to a process for the hydrogenation of imines with hydrogen under elevated pressure in the presence of hydrogen iodide.

U.S. Pat. No. 4,994,615 describes a process for the asymmetric hydrogenation of prochiral N-arylketimines wherein iridium catalysts having chiral diphosphine ligands are used. U.S. Pat. No. 5,011,995 describes a process for the asymmetric hydrogenation of prochiral N-alkylketimines using the same catalysts. U.S. Pat. No. 5,112,999 discloses polynuclear iridium compounds and a complex salt of iridium, which contain diphosphine ligands, as catalysts for the hydrogenation of imines.

Those homogeneous catalysis processes have proved valuable, although it is evident, especially in the case of relatively large batches or on an industrial scale, that the catalysts frequently tend to become deactivated to a greater or lesser extent depending on the catalyst precursor, the substrate and the diphosphine ligands that are used. In many cases, especially at elevated temperatures—for example at temperatures >25° C., which are necessary for a short reaction time—it is not possible to achieve complete conversion. For industrial applications of the hydrogenation processes, therefore, the catalyst productivity is too low to be economically viable.

It has now been found, surprisingly, that the catalyst activity can be increased by a factor of 10 or more if the reaction mixture contains hydrogen iodide. It has also unexpectedly been found that at the same time the deactivation of the catalysts can be considerably reduced or completely eliminated. It has also been found, surprisingly, that when asymmetric catalysts are used the enantioselectivity is high, and high optical yields of up to 80% can be achieved, even at reaction temperatures of more than 50° C.

The invention relates to a process for the hydrogenation of imines with hydrogen under elevated pressure in the presence of iridium catalysts and with or without an inert solvent, wherein the reaction mixture contains hydrogen iodide.

Suitable imines are especially those which contain at least one >C=N— group. If the groups are substituted asymmetrically and are thus compounds having a prochiral ketimine group, it is possible in the process according to the invention for mixtures of optical isomers or pure optical isomers to be formed if enantioselective or diastereo-selective iridium catalysts are used. The imines may contain further chiral carbon atoms. The free bonds in the above formulae may be saturated with hydrogen or organic radicals having from 1 to 22 carbon atoms or organic hetero radicals having from 1 to 20 carbon atoms and at least one hetero atom from the group O, S, N and P. The nitrogen atom of the group >C=N— may also be saturated with $NH_2$ or a primary amino group having from 1 to 22 carbon atoms or a secondary amino group having from 2 to 40 carbon atoms. The organic radicals may be substituted, for example, by F, Cl, Br, $C_1$–$C_4$haloalkyl wherein halogen is preferably F or Cl, —CN, —$NO_2$, —$CO_2H$, —$CONH_2$, —$SO_3H$, —$PO_3H_2$, or $C_1$–$C_{12}$alkyl esters or amides, or by phenyl esters or benzyl esters of the groups —$CO_2H$, —$SO_3H$ and —$PO_3H_2$. Aldimine and ketimine groups are especially reactive, with the result that using the process according to the invention it is possible selectively to hydrogenate >C=N— groups in addition to the >C=C< and/or >C=O groups. Aldimine and ketimine groups are also to be understood to include >C=N—N— hydrazone groups.

The process according to the invention is suitable especially for the hydrogenation of aldimines, ketimines and hydrazones with the formation of corresponding amines and hydrazines, respectively. The ketimines are preferably N-substituted. It is preferable to use chiral iridium catalysts and to hydrogenate enantiomerically pure, chiral or prochiral ketimines to prepare optical isomers, the optical yields (enantiomeric excess, ee) being, for example, higher than 30%, especially higher than 50%, and yields of more than 90% being achievable. The optical yield indicates the ratio of the two stereoisomers formed, which ratio may be, for example, greater than 2:1 and preferably greater than 4:1.

The imines are preferably imines of formula I

which are hydrogenated to form amines of formula II

wherein $R_3$ is preferably a substituent and wherein $R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_6$; a $C_7$–$C_{16}$aralkyl bonded via an alkyl carbon atom, or $C_1$–$C_{12}$alkyl substituted by the mentioned cycloalkyl or heterocycloalkyl or heteroaryl;

or wherein $R_3$ is $C_6$–$C_{12}$aryl, or $C_4$–$C_{11}$heteroaryl bonded via a ring carbon atom and having 1 or 2 hetero atoms in the ring; $R_3$ being unsubstituted or substituted by —CN, —$NO_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_4R_5$ or by —$COOR_4$, and the aryl radicals and the aryl groups in the aralkyl, aralkoxy and aralkylthio in turn being unsubstituted or substituted by —CN, —$NO_2$, F, Cl, $C_1$–$C_4$-alkyl, -alkoxy or -alkylthio, —OH, —$CONR_4R_5$ or by —$COOR_4$;

$R_4$ and $R_5$ are each independently of the other hydrogen, $C_1$–$C_{12}$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —$CONR_4R_5$ or by —$COOR_4$; $C_6$–$C_{12}$aryl or $C_7$–$C_{16}$aralkyl that is unsubstituted or substituted as $R_3$, or —$CONR_4R_5$ or —$COOR_4$, wherein $R_4$ and $R_5$ are as defined herein-before; or $R_3$ is as defined hereinbefore and $R_1$ and $R_2$ together are alkylene having from 2 to 5 carbon atoms that is optionally interrupted by 1 or 2 —O—, —S— or —$NR_6$- radicals, and/or unsubstituted or substituted by =O or as $R_1$ and $R_2$ above in the meaning of alkyl, and/or condensed with benzene, pyridine, pyrimidine, furan, thiophene or pyrrole; or $R_2$ is as defined hereinbefore and $R_1$ and $R_3$ together are alkylene having from 2 to 5 carbon atoms that is optionally interrupted by 1 or 2 —O—, —S— or —$NR_6$- radicals, and/or unsubstituted or substituted by =O or as $R_1$ and $R_2$ above in the meaning of alkyl, and/or condensed with benzene, pyridine, pyrimidine, furan, thiophene or pyrrole.

The radicals $R_1$, $R_2$ and $R_3$ may contain one or more chirality centres.

$R_1$, $R_2$ and $R_3$ can be substituted in any desired positions by identical or different radicals, for example by from 1 to 5, preferably from 1 to 3, substituents.

Suitable substituents for $R_1$ and $R_2$ and $R_3$ are: $C_1-C_{12}$-, preferably $C_1-C_6$-, and especially $C_1-C_4$-alkyl, -alkoxy or -alkylthio, e.g. methyl, ethyl, propyl, n-, iso- and tert-butyl, the isomers of pentyl, hexyl, octyl, nonyl, decyl, undecyl and dodecyl, and corresponding alkoxy and alkylthio radicals;

$C_1-C_6$haloalkyl, preferably $C_1-C_4$haloalkyl, having preferably F and Cl as halogen, e.g. trifluoro- or trichloro-methyl, difluorochloromethyl, fluorodichloromethyl, 1,1-difluoroeth-1-yl, 1,1-dichloroeth-1-yl, 1,1,1-trichloro- or 1,1,1-trifluoro-eth-2-yl, pentachloroethyl, pentafluoroethyl, 1,1,1-trifluoro-2,2-dichloroethyl, n-perfluoropropyl, iso-perfluoropropyl, n-perfluorobutyl, fluoro- or chloro-methyl, difluoro- or dichloro-methyl, 1-fluoro- or 1-chloro-eth-2-yl or -eth-1-yl, 1-, 2- or 3-fluoro- or 1-, 2- or 3-chloro-prop-1-yl or -prop-2-yl or -prop-3-yl, 1-fluoro- or 1-chloro-but-1-yl, -but-2-yl, -but-3-yl or -but4-yl, 2,3-dichloro-prop-1-yl, 1-chloro-2-fluoro-prop-3-yl, 2,3-dichlorobut-1-yl;

$C_6-C_{12}$-aryl, -aryloxy or -arylthio, in which aryl is preferably naphthyl and especially phenyl, $C_7-C_{16}$-aralkyl, -aralkoxy and -aralkylthio, in which the aryl radical is preferably naphthyl and especially phenyl and the alkylene radical is linear or branched and contains from 1 to 10, preferably from 1 to 6 and especially from 1 to 3, carbon atoms, for example benzyl, naphthylmethyl, 1- or 2-phenyl-eth- 1-yl or -eth-2-yl, 1-, 2- or 3-phenyl-prop-1-yl, -prop-2-yl or -prop-3-yl, with benzyl being especially preferred;

the radicals containing the aryl groups mentioned above may in turn be mono- or poly-substituted, for example by $C_1-C_4$-alkyl, -alkoxy or -alkylthio, halogen, —OH, —$CONR_4R_5$ or by —$COOR_5$, wherein $R_4$ and $R_5$ are as defined; examples are methyl, ethyl, n- and isopropyl, butyl, corresponding alkoxy and alkylthio radicals, F, Cl, Br, dimethyl-, methylethyl- and diethyl-carbamoyl and methoxy-, ethoxy-, phenoxy- and benzyloxy-carbonyl;

halogen, preferably F and Cl;

secondary amino having from 2 to 24, preferably from 2 to 12 and especially from 2 to 6 carbon atoms, the secondary amino preferably containing two alkyl groups, for example dimethyl-, methylethyl-, diethyl-, methylpropyl-, methyl-n-butyl-, di-n-propyl-, di-n-butyl-, di-n-hexyl-amino;

—$CONR_4R_5$, wherein $R_4$ and $R_5$ are each independently of the other $C_1-C_{12}$-, preferably $C_1-C_6$-, and especially $C_1-C_4$-alkyl, or $R_4$ and $R_5$ together are tetra- or penta-methylene or 3-oxapentylene, the alkyl being linear or branched, e.g. dimethyl-, methylethyl-, diethyl-, methyl-n-propyl-, ethyl-n-propyl-, di-n-propyl-, methyl-n-butyl-, ethyl-n-butyl-, n-propyl-n-butyl-and di-n-butyl-carbamoyl;

—$COOR_4$, wherein $R_4$ is $C_1-C_{12}$-, preferably $C_1-C_6$-alkyl, which may be linear or branched, e.g. methyl, ethyl, n- and iso-propyl, n-, iso- and tert-butyl, and the isomers of pentyl, hexyl, heptyl, octyl, nonyl, decyl, undecyl and dodecyl.

$R_1$ $R_2$ and $R_3$ may contain especially functional groups, such as keto groups, —CN, —$NO_2$, carbon double bonds, N—O—, aromatic halogen groups and amide groups.

$R_1$ and $R_2$ as heteroaryl are preferably a 5- or 6-membered ring having 1 or 2 identical or different hetero atoms, especially O, S or N, which contains preferably 4 or 5 carbon atoms and can be condensed with benzene. Examples of heteroaromatics from which $R_1$ can be derived are furan, pyrrole, thiophene, pyridine, pyrimidine, indole and quinoline.

$R_1$ and $R_2$ as heteroaryl-substituted alkyl are derived preferably from a 5- or 6-membered ring having 1 or 2 identical or different hetero atoms, especially O, S or N, which contains preferably 4 or 5 carbon atoms and can be condensed with benzene. Examples of heteroaromatics are furan, pyrrole, thiophene, pyridine, pyrimidine, indole and quinoline.

$R_1$ and $R_2$ as heterocycloalkyl or as heterocycloalkyl-substituted alkyl contain preferably from 4 to 6 ring atoms and 1 or 2 identical or different hetero atoms from the group O, S and $NR_6$. It can be condensed with benzene. It may be derived, for example, from pyrrolidine, tetrahydrofuran, tetrahydrothiophene, indane, pyrazolidine, oxazolidine, piperidine, piperazine or morpholine.

$R_1$, $R_2$ and $R_3$ as alkyl are preferably unsubstituted or substituted $C_1-C_6$-, especially $C_1-C_4$-alkyl, which may be linear or branched. Examples are methyl, ethyl, iso- and n-propyl, iso-, n- and tert-butyl, the isomers of pentyl, hexyl, heptyl, octyl, nonyl, decyl, undecyl and dodecyl.

$R_1$, $R_2$ and $R_3$ as unsubstituted or substituted cycloalkyl contain preferably from 3 to 6, especially 5 or 6, ring carbon atoms. Examples are cyclopropyl, cyclobutyl, cyclopentyl, cyclohexyl, cycloheptyl and cyclooctyl.

$R_1$, $R_2$ and $R_3$ as aryl are preferably unsubstituted or substituted naphthyl and especially phenyl. $R_1$, $R_2$ and $R_3$ as aralkyl are preferably unsubstituted or substituted phenylalkyl having from 1 to 10, preferably from 1 to 6 and especially from 1 to 4 carbon atoms in the alkylene, the alkylene being linear or branched. Examples are especially benzyl, and 1-phenyleth-1-yl, 2-phenyleth-1-yl, 1-phenylprop-1-yl, 1-phenylprop-2-yl, 1-phenyl-prop-3-yl, 2-phenylprop-1-yl, 2-phenylprop-2-yl and 1-phenylbut4-yl.

In $R_2$ and $R_3$ as —$CONR_4R_5$ and —$COOR_4$, $R_4$ and $R_5$ are preferably $C_1-C_6$-, especially $C_1-C_4$-alkyl, or $R_4$ and $R_5$ together are tetramethylene, pentamethylene or 3-oxapentylene. Examples of alkyl are mentioned hereinbefore.

$R_1$ and $R_2$ together or $R_1$ and $R_3$ together as alkylene are preferably interrupted by one —O—, —S— or —$NR_6$-radical, preferably —O—. $R_1$ and $R_2$ together or $R_1$ and $R_3$ together form, with the carbon atom or with the —N=C group to which they are bonded, respectively, preferably a 5- or 6-membered ring. For the substituents the preferences mentioned herein-before apply. As condensed alkylene, $R_1$ and $R_2$ together or $R_1$ and $R_3$ together are preferably alkylene condensed with benzene or pyridine. Examples of alkylene are: ethylene, 1,2- or 1,3-propylene, 1,2-, 1,3- or 1,4-butylene, 1,5-pentylene and 1,6-hexylene. Examples of interrupted or =O-substituted alkylene are 2-oxa-1,3-propylene, 2-oxa-1,4-butylene, 2-oxa- or 3-oxa- 1,5-pentylene, 3-thia- 1,5-pentylene, 2-thia- 1,4-butylene, 2-thia-1,3-propylene, 2-methylimino-1,3-propylene, 2-ethylimino-1,4-butylene, 2- or 3-methylimino-1,5-pentylene, 1-oxo-2-oxa- 1,3-propylene, 1-oxo-2-oxa- 1,4-butylene, 2-oxo-3-oxa-1,4-butylene, 1-oxa-2-oxo- 1,5-pentylene. Examples of condensed alkylene are:

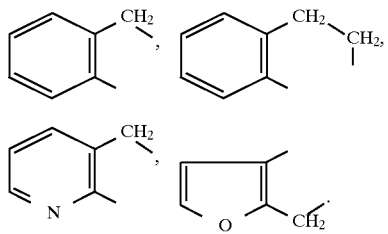

Examples of condensed and interrupted and unsubstituted or =O-substituted alkylene are:

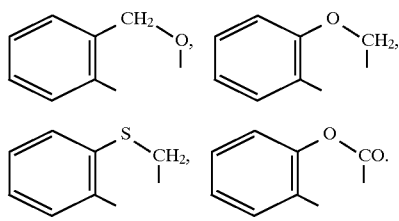

$R_4$ and $R_5$ are preferably each independently of the other hydrogen, $C_1$–$C_4$alkyl, phenyl or benzyl. $R_6$ is preferably hydrogen or $C_1$–$C_4$alkyl.

A further preferred group is formed by prochiral imines in which in formula I $R_1$, $R_2$ and $R_3$ are each different from the others and are not hydrogen.

In an especially preferred group, in formula I $R_3$ is 2,6-di-$C_1$–$C_4$alkylphen-1-yl and especially 2,6-dimethylphen-1-yl or 2-methyl-6-ethylphen-1-yl, $R_1$ is $C_1$–$C_4$alkyl and especially ethyl or methyl, and $R_2$ is $C_1$–$C_4$alkyl, $C_1$–$C_4$alkoxymethyl or $C_1$–$C_4$alkoxyethyl, and especially methoxymethyl.

Of those compounds, imines of formulae

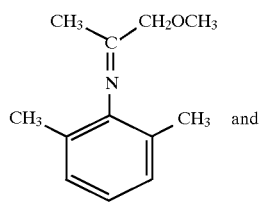 (Va)

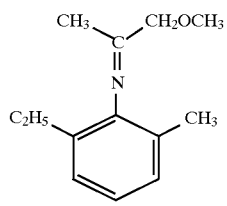 (Vb)

important, as is the imine of the formula

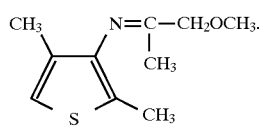 (Vc)

Imines of formula I are known or they can be prepared in accordance with known processes from aldehydes or ketones and primary amines.

The iridium catalysts are preferably homogeneous catalysts that are substantially soluble in the reaction medium. The term "catalyst" also includes catalyst precursors that are converted into an active catalyst species at the beginning of a hydrogenation. The catalysts preferably correspond to formulae III, IIIa, IIIb, IIIc and IIId,

[XIrYZ] (III),

[XIrY]$^\oplus$A$^\ominus$ (IIIa),

[YIrZ$_4$]$^\ominus$M$^\oplus$ (IIIb),

[YIrHZ$_2$]$_2$ (IIIc) and

[YIrZ$_3$]$_2$ (IIId), wherein X is two olefin ligands or a diene ligand, Y is a ditertiary diphosphine (a) the phosphine groups of which are bonded to different carbon atoms of a carbon chain having from 2 to 4 carbon atoms, or (b) the phosphine groups of which are either bonded directly or via a bridge group —$CR_aR_b$- in the ortho positions of a cyclopentadienyl ring or are each bonded to a cyclopentadienyl ring of a ferrocenyl, or (c) one phosphine group of which is bonded to a carbon chain having 2 or 3 carbon atoms and the other phosphine group of which is bonded to an oxygen atom or a nitrogen atom bonded terminally to that carbon chain, or (d) the phosphine groups of which are bonded to the two oxygen atoms or nitrogen atoms bonded terminally to a $C_2$-carbon chain; with the result that in the cases of (a), (b), (c) and (d) a 5-, 6- or 7-membered ring is formed with the Ir atom, the radicals Z are each independently of the other(s) Cl, Br or I, $A^\ominus$ is the anion of an oxy or complex acid, and $M^\oplus$ is an alkali metal cation or quaternary ammonium, and $R_a$ and $R_b$ are each independently of the other hydrogen, $C_1$–$C_8$alkyl, $C_1$–$C_4$fluoroalkyl, phenyl or benzyl or are phenyl or benzyl having from 1 to 3 $C_1$–$C_4$alkyl or $C_1$–$C_4$alkoxy substituents. $R_b$ is preferably hydrogen. $R_a$ is preferably C1—$C_4$alkyl and especially methyl.

The diphosphine Y contains preferably at least one chiral group and the diphosphine is especially an optically pure stereoisomer, or a pair of diastereoisomers, since the use of catalysts containing chiral ligands leads to optical induction in asymmetric hydrogenation.

X as an olefin ligand may be a branched or, preferably, linear $C_2$–$C_{12}$alkylene, especially $C_2$–$C_6$alkylene. Some examples are dodecylene, decylene, octylene, 1-, 2- or 3-hexene, 1-, 2- or 3-pentene, 1- or 2-butene, propene and ethene. X as a diene ligand may be an open-chain or cyclic diene having from 4 to 12, preferably from 5 to 8, carbon atoms, the diene groups preferably being separated by one or two saturated carbon atoms. Some examples are butadiene, pentadiene, hexadiene, heptadiene, octadiene, decadiene, dodecadiene, cyclopentadiene, cyclohexadiene, cycloheptadiene, cyclooctadiene and bridged cyclodienes such as norbornadiene and bicyclo-2,2,2-octadiene. Hexadiene, cyclooctadiene and norbornadiene are preferred.

The phosphine groups contain preferably two identical or different, preferably identical, unsubstituted or substituted hydrocarbon radicals having from 1 to 20, especially from 1 to 12 carbon atoms. Preference is given to diphosphines wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$-cycloalkyl, $C_5$–$C_{12}$cycloalkyl-$CH_2$-, phenyl or benzyl; and phenyl or benzyl substituted by halogen (e.g. F, Cl or Br), $C_1$–$C_6$haloalkyl, $(C_1$–$C_{12}$alkyl$)_3$Si, $(C_6H_5)_3$Si, $C_1$–$C_6$haloalkoxy (e.g. trifluoromethoxy), —$NH_2$, phenyl$_2$N-, benzyl$_2$N-, morpholinyl, piperidinyl, pyrrolidinyl, $(C_1$–$C_{12}$alkyl$)_2$N-, -ammonium-$X_1^\ominus$, —$SO_3M_1$, —$CO_2M_1$, —$PO_3M_1$ or by —COO-$C_1$–$C_6$-alkyl (e.g. —$COOCH_3$), wherein $M_1$ is an alkali metal or hydrogen and $X_1^\oplus$ is the anion of a monobasic acid. $M_1$ is preferably hydrogen, Li, Na or K. $A_1^\ominus$, as the anion of a mono-basic acid, is preferably $Cl^\ominus$, $Br^\oplus$ or the anion of a carboxylic acid, for example formate, acetate, trichloroacetate or trifluoroacetate.

A secondary phosphine group may also be a radical of the formula

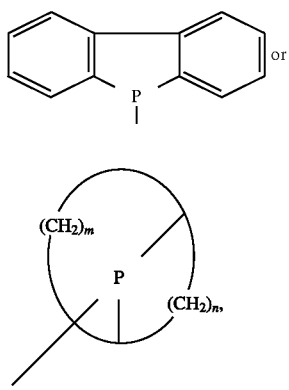

wherein
m and n are each independently of the other an integer from 2 to 10, and the sum of m+n is from 4 to 12, especially from 5 to 8. Examples thereof are [3.3.1]- and [4.2.1]-phobyl of the formulae

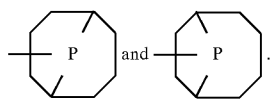

A secondary phosphine group may also be a radical of the formula

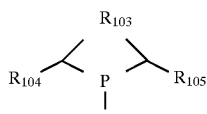

wherein $R_{103}$ is $C_1$–$C_4$alkylene, preferably $C_2$- or $C_3$-alkylene, and $R_{104}$ and $R_{105}$ are each independently of the other hydrogen, $C_1$–$C_6$alkyl, $C_1$–$C_6$alkoxy, $C_1$–$C_6$haloalkyl, $C_5$- or $C_6$-cycloalkyl, unsubstituted or $C_1$–$C_4$alkyl-, $C_1$–$C_4$alkoxy-, $C_1$–$C_4$haloalkyl- or halo-substituted phenyl, or unsubstituted or $C_1$–$C_4$alkyl-, $C_1$–$C_4$alkoxy-, $C_1$–$C_4$haloalkyl- or halo-substituted benzyl. $R_{104}$ and $R_{105}$ may be, for example, methyl, ethyl, n- or isopropyl, n-, iso- or tert-butyl, cyclohexyl, phenyl or benzyl. Halogen is preferably F or Cl. Such phosphine groups have further chiral carbon atoms and can be used in the form of racemates or diastereoisomers. Of such phosphine ligands, those of the formula

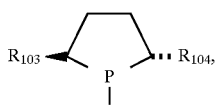

wherein $R_{103}$ and $R_{104}$ are $C_1$–$C_4$alkyl or phenyl, are especially preferred.

Examples of alkyl that preferably contains from 1 to 6 carbon atoms are methyl, ethyl, n-propyl, isopropyl, n-, iso- and tert-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of alkyl-, alkoxy- or haloalkoxy-substituted phenyl and benzyl are methylphenyl, dimethylphenyl, trimethylphenyl, ethylphenyl, methylbenzyl, methoxyphenyl, dimethoxyphenyl, trifluoromethylphenyl, bis-tri-fluoromethylphenyl, tris-trifluoromethylphenyl, trifluoromethoxyphenyl and bis-trifluoro-methoxyphenyl. Preferred phosphine groups are those having identical or different, preferably identical, radicals from the group $C_1$–$C_6$alkyl; cyclopentyl and cyclohexyl that are unsubstituted or have from 1 to 3 $C_1$–$C_4$alkyl or $C_1$–$C_4$alkoxy substituents, and benzyl and, especially, phenyl that is unsubstituted or has from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

Y as a diphosphine preferably corresponds to formula IV, IVa, IVb, IVc or IVd, $$R_7R_8P\text{-}R_9\text{-}PR_{10}R_{11} \qquad (IV),$$

$$R_7R_8P\text{-}O\text{-}R_{12}\text{-}PR_{10}R_{11} \qquad (IVa),$$

$$R_7R_8P\text{-}NR_c\text{-}R_{12}\text{-}PR_{10}R_{11} \qquad (IVb),$$

$$R_7R_8P\text{-}O\text{-}R_{13}\text{-}O\text{-}PR_{10}R_{11} \qquad (IVc),$$

$$R_7R_8P\text{-}NR_c\text{-}R_{13}\text{-}NR_c\text{-}PR_{10}R_{11} \qquad (IVd),$$

wherein
$R_7$, $R_8$, $R_{10}$ and $R_{11}$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N-, benzyl$_2$N-, morpholinyl, piperidinyl, pyrrolidinyl, $(C_1$—$C_{12}$alkyl$)_2$N-, -ammonium-$X_1^\ominus$, —$SO_3M_1$, —$CO_2M_1$, —$PO_3M_1$ or by —COO-$C_1$–$C_6$alkyl, wherein $M_1$ is an alkali metal or hydrogen and $X_1^\ominus$ is the anion of a monobasic acid;

$R_9$ is linear $C_2$–$C_4$alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cyclo-alkenylene, -bicycloalkylene or -bicycloalkenylene having from 4 to 10 carbon atoms, each of which is unsubstituted or substituted by $C_1$–$C_6$alkyl, phenyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 1,4-butylene substituted in the 2,3-positions by

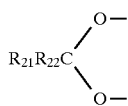

and unsubstituted or substituted in the 1,4-positions by $C_1$–$C_6$alkyl, phenyl or by benzyl, wherein $R_{21}$ and $R_{22}$ are each independently of the other hydrogen, $C_1$–$C_6$alkyl, phenyl or benzyl; 3,4- or 2,4-pyrrolidinylene or 2-methylene-pyrrolidin4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-xylylene, 1,8-naphthylene, 2,2'-dinaphthylene or 2,2'-diphenylene, each of which is unsubstituted or substituted by $C_1$–$C_4$alkyl;

or $R_9$ is a radical of the formula

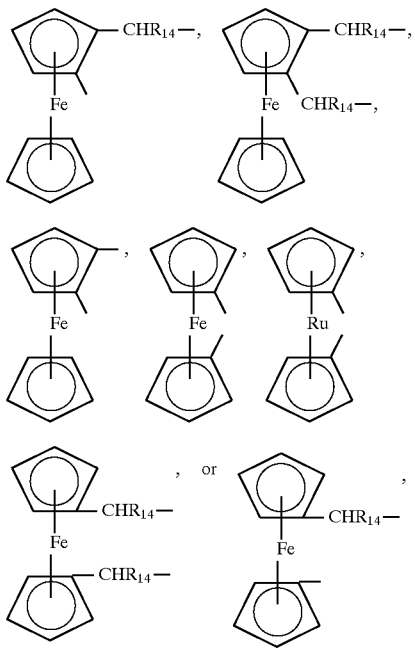

wherein $R_{14}$ is hydrogen, $C_1$–$C_8$alkyl, $C_1$–$C_4$fluoroalkyl, phenyl or phenyl having from 1 to 3 $C_1$–$C_4$alkyl or $C_1$–$C_4$alkoxy substituents;

$R_{12}$ is linear $C_2$- or $C_3$-alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cyclo-alkenylene, -bicycloalkylene or -bicycloalkenylene having from 4 to 10 carbon atoms, each of which is unsubstituted or substituted by $C_1$–$C_6$alkyl, phenyl or by benzyl; or 1,2-or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 3,4- or 2,4-pyrrolidinylene or 3-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_2$alkylaminocarbonyl; or 1,2-phenylene, 2-benzylene, 1,2-, 2,3- or 1,8-naphthylene, each of which is unsubstituted or substituted by $C_1$–$C_4$alkyl; and $R_{13}$ is linear $C_2$alkylene that is unsubstituted or substituted by $C_1$–$C_6$alkyl, $C_5$- or $C_6$-cycloalkyl, phenyl, naphthyl or by benzyl; 1,2ycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; 3,4-pyrrolidinylene the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene that is unsubstituted or substituted by $C_1$–$C_4$alkyl, or is a radical, less two hydroxy groups in the ortho positions, of a mono- or di-saccharide, and $R_C$ is hydrogen, $C_1$–$C_4$alkyl, phenyl or benzyl.

$R_7$, $R_8$, $R_{10}$ and $R_{11}$ are preferably identical or different, preferably identical, radicals from the following group: $C_1$–$C_6$alkyl; cyclopentyl and cyclohexyl that are unsubstituted or have from one to three $C_1$–$C_4$alkyl or $C_1$–$C_4$alkoxy substituents, and benzyl and, especially, phenyl that is unsubstituted or has from one to three $C_1$–$C_4$alkyl, $C_1$–$C_4$alkoxy, F, Cl, $C_1$–$C_4$fluoroalkyl or $C_1$–$C_4$fluoroalkoxy substituents.

A preferred subgroup of diphosphines Y is formed by those of the formulae

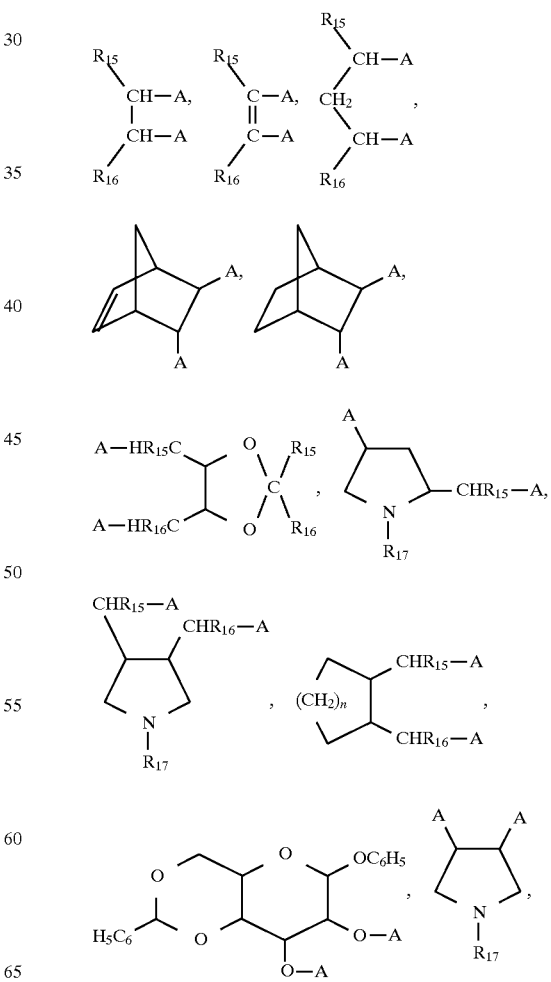

-continued

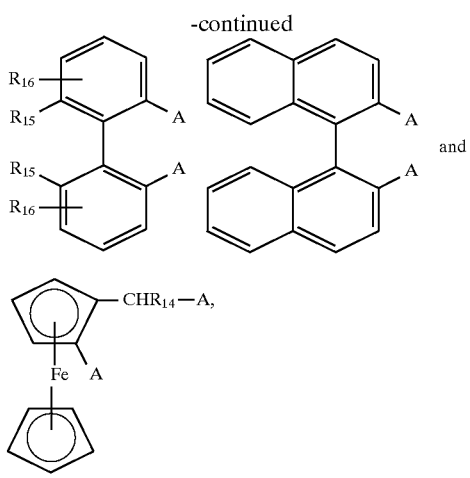

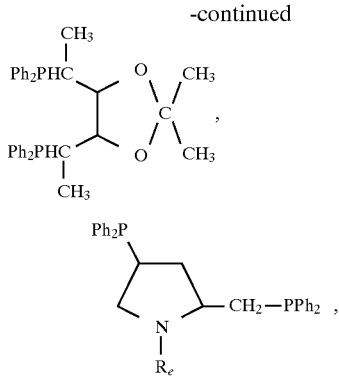 and wherein $R_{15}$ and $R_{16}$ are each independently of the other hydrogen, $C_1$–$C_4$alkyl, phenyl, benzyl, or phenyl or benzyl having from one to three $C_1$–$C_4$alkyl or $C_1$–$C_4$alkoxy substituents, $R_{14}$ is hydrogen, $C_1$–$C_4$alkyl, phenyl, benzyl, or phenyl or benzyl having from one to three $C_1$–$C_4$alkyl or $C_1$–$C_4$alkoxy substituents, $R_{17}$ is hydrogen, $C_1$–$C_4$alkyl, phenyl, benzyl, $C_1$–$C_6$alkoxy-CO-, $C_1$–$C_6$alkyl-CO-, phenyl-CO-, naphthyl-CO- or $C_1$–$C_4$alkylNH-CO-, A may be identical or different groups —P(R)$_2$, wherein R is $C_1$–$C_6$alkyl, cyclohexyl, phenyl, benzyl, or phenyl or benzyl having from one to three $C_1$–$C_4$alkyl, disubstituted amino, $C_1$–$C_4$alkoxy, —CF$_3$ or partially or fully fluorinated $C_1$–$C_4$alkoxy substituents, and n is 0, 1 or 2. Of those phosphines, chirally substituted compounds are especially preferred.

Some preferred examples of diphosphines Y are as follows (Ph is phenyl):

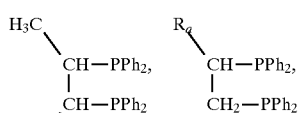

$R_a$ = methyl, cyclohexyl, phenyl

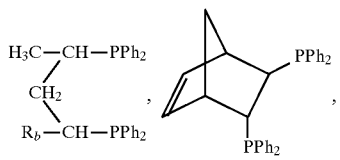

$R_b$ = H, methyl

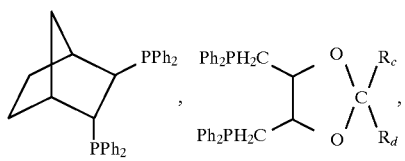

$R_c$ = H, methyl, phenyl
$R_d$ = H, methyl, phenyl

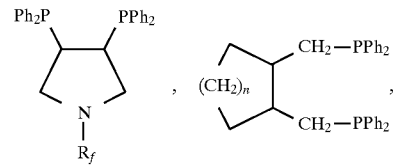

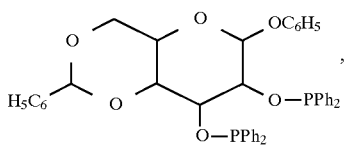

$R_e$ = —CO$_2$-tert-butyl, —CO-tert-butyl, H, —CO-phenyl, —CO—NH—C$_1$–C$_4$ alkyl

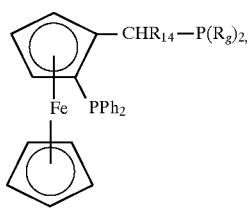

$R_f$ = $C_1$–$C_4$ alkyl, benzyl    n = 0, 1 or 2

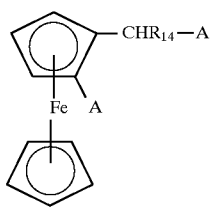

wherein $R_{14}$ is $C_1$–$C_4$alkyl, especially methyl and $R_g$ is phenyl or cyclohexyl that is unsubstituted or has from one to three methyl, disubstituted amino, —CF$_3$ or methoxy substituents.

Especially suitable diphosphine ligands Y are those wherein the secondary phosphine groups are either bonded directly or via a bridge group —CR$_a$R$_b$- in the ortho positions of a cyclopentadienyl ring or are each bonded to a cyclopentadienyl ring of a ferrocenyl, more especially those of formula X wherein $R_{14}$ is hydrogen, $C_1$–$C_4$alkyl, phenyl, benzyl, or phenyl or benzyl substituted by from one to three $C_1$–$C_4$alkyl or $C_1$–$C_4$alkoxy substituents, A represents identical or different groups —P(R)$_2$ wherein R is $C_1$–$C_6$alkyl, cyclohexyl, phenyl, benzyl, or phenyl or benzyl substituted by from one to three $C_1$–$C_4$alkyl, disubstituted amino, $C_1$–$C_4$alkoxy, —CF$_3$ or partially or fully fluorinated $C_1$–$C_4$alkoxy substituents.

Preference is given to a sub-group wherein the diphosphine of formula X is chiral and $R_{14}$ is $C_1$–$C_4$alkyl, or is phenyl or benzyl substituted by from one to three $C_1$–$C_4$alkyl or $C_1$–$C_4$alkoxy substituents, A represents identical or different groups —P(R)$_2$ wherein R is $C_1$–$C_6$alkyl, cyclohexyl, phenyl, benzyl, or phenyl or benzyl substituted by from one to three $C_1$–$C_4$alkyl, disubstituted amino, $C_1$–$C_4$alkoxy, —CF$_3$ or partially or fully fluorinated $C_1$–$C_4$alkoxy substituents.

Very special preference is given to the following disphosphine ligands which can be used especially in catalysts of formula (III):

{(R)-1-[(S)-2-diphenylphosphino)ferrocenyl]}ethyl-di(3,5-dimethyl-phenyl)phosphine, {(R)-1-[(S)-2-diphenylphosphino)ferrocenyl]}ethyl-di(3,5-dimethyl-4-N,N-dipropyl-aminophenyl)phosphine, {(R)-1-[(S)-2-diphenylphosphino)ferrocenyl]}ethyl-di(3,5-di-iso-propyl4-N,N-dimethyl-aminophenyl)phosphine, {(R)-1-[(S)-2-diphenylphosphino)ferrocenyl]}ethyl-di(3,5-di-iso-propyl4-N,N-di-benzylylaminophenyl)phosphine, {(R)-1-[(S)-2-diphenylphosphino)ferrocenyl]}ethyl-di(3,5-dimethyl4-N,N-dibenzylyl-aminophenyl)phosphine, {(R)-1-[(S)-2-diphenylphosphino)ferrocenyl]}ethyl-di(3,5-dimethyl4-( 1'-pyrrolo)-phenyl)phosphine, {(R)-1[(S)-2-diphenylphosphino)ferrocenyl]}ethyl-di(3,5-dimethyl-4N,N-dipentyl-aminophenyl)phosphine, {(R)-1-[(S)-2-diphenylphosphino)ferrocenyl]}ethyl-di(3,5-dimethyl-4-N,N-dimethyl-aminophenyl)phosphine, 1,4-bis(diphenylphosphino)butane, {(R)-1[(S)-2-di(4-methoxyphenyl)phosphino)ferrocenyl]}ethyl-di(3,5-dimethyl-4-N,N-dimethylaminophenyl) phosphine and especially {(R)-1-[(S)-2-diphenylphosphino)ferrocenyl]}ethyl-di(3,5-dimethyl-phenyl)phosphine.

Suitable diphosphines and diphosphinites have been described, for example, by H. B. Kagan in Chiral Ligands for Asymmetric Catalysis, Asymmetric Synthesis, Volume 5, pp. 13–23, Academic Press Inc., N.Y. (1985). The preparation of ferrocenyl diphosphine ligands is described, for example, in EP-A-0 564 406 and by T. Hayashi et al. in Bull. Chem. Soc. Jpn., 53, pages 1136–1151.

$A^\ominus$ in formula IIIa can be derived from inorganic or organic oxy acids. Examples of such acids are $H_2SO_4$, $HClO_4$, $HClO_3$, $HBrO_4$, $HIO_4$, $HNO_3$, $H_3PO_3$, $H_3PO_4$, $CF_3SO_3H$, $C_6H_5SO_3H$, $CF_3COOH$ and $CCl_3COOH$. Complex acids from which $A^\ominus$ can be derived are, for example, the halo complex acids of the elements B, P, As, Sb and Bi. Preferred examples of $A^\ominus$ in formula IIIa are $ClO_4^\ominus$, $CF_3SO_3^\ominus$, $BF_4^\ominus$, $B(phenyl)_4^\ominus$, $PF_6^\ominus$, $SbCl_6^\ominus$, $AsF_6^\ominus$ and $SbF_6^\ominus$.

When $M^\oplus$ in formula IIIb is an alkali metal cation, it may be, for example, a Li, Na, K, Rb or Cs cation. When $M^\oplus$ is quaternary ammonium, it may contain a total of from 4 to 40, preferably from 4 to 24, carbon atoms. $M^\oplus$ may correspond to the formula phenyl-$N^\oplus(C_1$–$C_6$alkyl)$_3$, benzyl$N^\oplus(C_1$–$C_6$alkyl)$_3$ or $(C_1$–$C_6$alkyl)$_4N^\oplus$. $M^\oplus$ in formula IIIb is preferably $Li^\oplus$, $Na^\oplus$ or $K^\oplus$ or $(C_1$–$C_6$alkyl)$_4N^\oplus$.

Z in formula III is preferably Br or Cl and especially Cl. Z in formula IIIb is preferably Br or I and Z in formulae IIIc and IIId is preferably I.

The preparation of the catalysts is known per se and is described, for example, in U.S. Pat. No. 4,994,615, U.S. Pat. No. 5,011,995, U.S. Pat. No. 5,112,999 and EP-A-0 564 406.

The preparation of the catalysts of formula III can be carried out, for example, by reacting a diiridium complex of the formula [IrXZ]$_2$ with a diphosphine Y. The iridium catalysts can be added to the reaction mixture as isolated compounds. It has proved advantageous, however, to produce the catalysts in situ with or without a solvent prior to the reaction and to add optionally a portion or all of the acid and of an ammonium or alkali metal halide.

The molar ratio of imine to iridium catalyst may be, for example, from 5 000 000 to 10, especially from 2 000 000 to 20, more preferably from 1 000 000 to 100, and more especially from 1 000 000 to 1000.

The molar ratio of imine to hydrogen iodide is, for example, from 1 000 000 to 100, preferably from 500 000 to 500, more especially from 10 000 to 1000.

In a preferred procedure, the ratio of hydrogen iodide to iridium is from 200 to 1.

The process is carried out preferably at a temperature of from −20° to 100° C., especially from 0° to 80° C. and more especially from 10° to 70° C., and preferably at a hydrogen pressure of $2 \times 10^5$ to $1.5 \times 10^7$ Pa (5 to 150 bar), especially $10^6$ to $10^7$ Pa (10 to 100 bar).

The reaction can be carried out in the absence or in the presence of solvents. Examples of suitable solvents, which can be used alone or as a mixture of solvents, are:

aliphatic and aromatic hydrocarbons, such as pentane, hexane, cyclohexane, methylcyclohexane, benzene, toluene and xylene; ethers, such as diethyl ether, diethylene glycol dimethyl ether, tetrahydrofuran and dioxane; halogenated hydrocarbons, such as methylene chloride, chloroform, 1,1,2,2-tetrachloroethane and chlorobenzene; esters and lactones, such as ethyl acetate, butyrolactone and valerolactone; acid amides and lactams, such as dimethylformamide, dimethylacetamide and N-methylpyrrolidone, and ketones, such as acetone, dibutyl ketone, methyl isobutyl ketone and methoxyacetone.

Hydrogen iodide can be added in gaseous form or in the form of an aqueous solution or in the form of any solution. In some cases it may be advantageous to operate under anhydrous conditions.

In detail, the process according to the invention can be carried out by first preparing the catalyst by dissolving, for example, (Ir-dieneCl)$_2$ and a diphosphine in a solvent or a portion of the substance to be hydrogenated; then hydrogen iodide (in gaseous form or in the form of an aqueous solution) and imine (optionally in the form of a solution) are added. The mixture is hydrogenated in an autoclave and the reaction mixture is isolated and purified in a manner known per se, for example by precipitation, extraction or distillation. Prior to the hydrogenation it is expedient to operate under an inert gas. It is advantageous to ensure that the catalyst solution stands for only a short time, and to carry out the hydrogenation of the imines as soon as possible after the preparation of the catalyst solution.

In the case of the hydrogenation of aldimines and ketimines, the aldimines and ketimines can also be formed in situ before or during the hydrogenation. In a preferred form, an amine and an aldehyde or a ketone are mixed together and added to the catalyst solution and the aldimine or ketimine formed in situ is hydrogenated. It is also possible, however, to use an amine, a ketone or an aldehyde together with the catalyst as the initial batch and to add the ketone or the aldehyde or the amine thereto, either all at once or in metered amounts.

The hydrogenation can be carried out continuously or batchwise in various types of reactor. Preference is given to those reactors which allow comparatively good intermixing and good removal of heat, such as, for example, loop reactors. That type of reactor has proved to be especially satisfactory when small amounts of catalyst are used.

The process according to the invention yields the corresponding amines in short reaction times while having chemically a high degree of conversion, with surprisingly good optical yields (ee) of 70% or more being obtained even at relatively high temperatures of more than 50° C., and even with high molar ratios of imine to catalyst.

The hydrogenated organic compounds that can be prepared in accordance with the invention, for example the amines, are biologically active substances or are intermediates for the preparation of such substances, especially in the field of the preparation of pharmaceuticals and agrochemicals. For example, o,o-dialkylarylketamine derivatives, especially those having alkyl and/or alkoxyalkyl groups, are effective as fungicides, especially as herbicides. The derivatives may be amine salts, acid amides, for example of chloroacetic acid, tertiary amines and ammonium salts (see, for example, EP-A-0 077 755 and EP-A-0 115 470).

Especially important in this connection are the optically active amines of formula

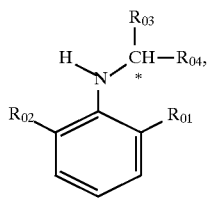
(VI)

which can be prepared from the imines of formula (V) in the presence of asymmetric iridium catalysts using the processes according to the invention, wherein $R_{01}$, $R_{02}$ and $R_{03}$ are each independently of the others $C_1$–$C_4$alkyl, and $R_{04}$ is $C_1$–$C_4$alkyl or $C_1$–$C_4$alkoxy-methyl or $C_1$–$C_4$alkoxyethyl, and especially the amines of formulae

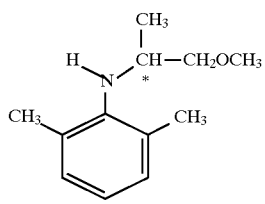
(VIa)

and

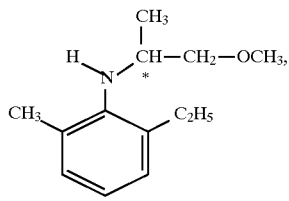
(VIb)

which can be prepared from the imines of formulae (Va) and (Vb) and which can be converted in accordance with methods that are customary per se with chloroacetic acid into the desired herbicides of the chloroacetanilide type; of those compounds, special preference is given to those having the S-configuration at the asymmetric C* atom.

The Examples that follow illustrate the invention in more detail. The chemical conversion is determined by gas chromatography [DB 17/30 W column (15 m), manufacturer: JCW Scientific Inc. USA, temperature programme: from 60° C./1 min to 220° C., ΔT: 10°•min$^{-1}$]. The optical yields (enantiomeric excess, ee) are determined either by gas chromatography [Chirasil-Val column, 50 m, manufacturer: Alltech, USA, T=150° C., isothermic], by HPLC (Chiracel OD column) or by $^1$H-NMR spectroscopy (using shift reagents).

EXAMPLE 1

Preparation of (S)-N-(2'-methyl-6'-ethyl-phen-1'-yl)-N-(1-methoxymethyl)-ethylamine.

1.44 mg (0.0021 mmol) of [Ir(1,5-cyclooctadiene)Cl]$_2$ and 2.87 mg (0.0045 mmol) of {(R)-1-[(S)-2-diphenylphosphino)ferrocenyl]}ethyl-di(3,5-dimethylphenyl)phosphine are dissolved in 12 g (58 mmol) of N-(2'-methyl-6'-ethyl-phen-1'-yl)-N-(1-methoxymethyl)eth-1-ylideneamine. In parallel, 92 mg (0.41 mmol) of hydrogen iodide in the form of a 57% aqueous solution are introduced into 400 g (1951 mmol) of N-(2'-methyl-6'-ethyl-phen-1'-yl)-N-(1-methoxymethyl)eth-1-ylideneamine and the mixture is stirred for 15 minutes. The two solutions are transferred to a steel autoclave and hydrogenated at 50° C. and 80 bar hydrogen pressure. After 6 hours the reaction is discontinued, cooled to room temperature and the reaction mixture is distilled at 10–15 mbar. 397 g (yield 96%) are obtained. (S)-N-(2'-Methyl-6'-ethyl-phen-1'-yl)-N-(1-methoxy-methyl)ethylamine in an optical yield of 76% ee (corresponding to an enantiomeric ratio S:R=88:12).

EXAMPLE 2

Preparation of (S)-N-(2',6'-dimethylphen-1'-yl)-N-(1-methoxymethyl)-ethylamine.

The procedure is as in Example 1, but the following compounds and amounts are used:

7.2 mg (0.0107 mmol) of [Ir(1,5-cyclooctadiene)Cl]$_2$, 14.4 mg (0.0225 mmol) of {(R)-1-[(S)-2-diphenylphosphino)ferrocenyl]}ethyl-di(3,5-dimethylphen-1'-yl)phosphine, 38.2 g (0.2 mol) of N-(2',6'-dimethylethyl-phen-1'-yl)-N-(1-methoxymethyl)ethylidene-amine and 0.8 ml of hydrogen iodide in the form of a 57% aqueous solution.

The reaction time is 3 hours, the conversion is 100% and the optical yield ee is 68% (S).

EXAMPLE 3

Preparation of (S)-N-(2',4'-dimethylthien-3'-yl)-N-(1-methoxymethyl)-ethylamine

The procedure is as in Example 1, but the following compounds and amounts are used:

8.6 mg (0.0128 mmol) of [Ir(1,5-cyclooctadiene)Cl]$_2$, 17.2 mg (0.026 mmol) of {(R)-1-[(S)-2-diphenylphosphino)ferrocenyl]}ethyl-di(3,5-dimethylphen-1'-yl)phosphine, 1 g (5.07 mmol) of N-(2',4'-dimethylthien-3'-yl)-N-(1-methoxymethyl)ethylideneamine and 0.07 ml of hydrogen iodide in the form of a 57% aqueous solution and 7 ml of toluene.

The pressure is 30 bar and the reaction temperature is 25° C. The reaction time is 2 hours, the conversion is 100% and the optical yield ee is 76.1% (S).

What is claimed is:

1. A process for the hydrogenation of an imine with hydrogen under elevated pressure in the presence of an iridium catalyst and with or without an inert solvent, wherein the reaction mixture contains hydrogen iodide.

2. A process according to claim 1, wherein the imine contains at least one >C=N— group.

3. A process according to claim 1, wherein the imine contains at least one of the groups >C=N— and >C=N—N— and additionally unsaturated groups >C=C< and >C=O.

4. A process according to claim 3, wherein the free bonds are saturated with hydrogen or organic radicals having from 1 to 22 carbon atoms or organic hetero radicals having from 1 to 20 carbon atoms and at least one hetero atom from the group O, S, N and P; or the nitrogen atom of the group >C=N— is saturated with $NH_2$ or a primary amino group having from 1 to 22 carbon atoms or a secondary amino group having from 2 to 40 carbon atoms.

5. A process according to claim 1, wherein an aldimine, ketimine or hydrazone is hydrogenated.

6. A process according to claim 5, wherein the imine is an imine of formula I

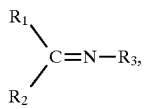 (I)

which is hydrogenated to form an amine of formula II

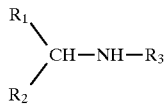 (II)

wherein $R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_6$; a $C_7$–$C_{16}$aralkyl bonded via an alkyl carbon atom, or $C_1$–$C_{12}$alkyl substituted by the mentioned cycloalkyl or heterocycloalkyl or heteroaryl;

or wherein $R_3$ is $C_6$–$C_{12}$aryl, or $C_4$–$C_{11}$heteroaryl bonded via a ring carbon atom and having 1 or 2 hetero atoms in the ring; $R_3$ being unsubstituted or substituted by —CN, —$NO_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_4R_5$ or by —$COOR_4$, and the aryl radicals and the aryl groups in the aralkyl, aralkoxy and aralkylthio in turn being unsubstituted or substituted by —CN, —$NO_2$, F, Cl, $C_1$–$C_4$-alkyl, -alkoxy or -alkylthio, —OH, —$CONR_4R_5$ or by —$COOR_4$;

$R_4$ and $R_5$ are each independently of the other hydrogen, $C_1$–$C_{12}$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, C1–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —$CONR_4R_5$ or by —$COOR_4$; $C_6$–$C_{12}$aryl or $C_7$–$C_{16}$aralkyl that is unsubstituted or substituted as $R_3$, or —$CONR_4R_5$ or —$COOR_4$, wherein $R_4$ and $R_5$ are as defined hereinbefore; or $R_3$ is as defined hereinbefore and $R_1$ and $R_2$ together are alkylene having from 2 to 5 carbon atoms that is optionally interrupted by 1 or 2 —O—, —S— or —$NR_6$- radicals, and/or unsubstituted or substituted by =O or as $R_1$ and $R_2$ above in the meaning of alkyl, and/or condensed with benzene, pyridine, pyrimidine, furan, thiophene or pyrrole; or $R_2$ is as defined hereinbefore and $R_1$ and $R_3$ together are alkylene having from 2 to 5 carbon atoms that is optionally interrupted by 1 or 2 —O—, —S— or —$NR_6$- radicals, and/or unsubstituted or substituted by =O or as $R_1$ and $R_2$ above in the meaning of alkyl, and/or condensed with benzene, pyridine, pyrimidine, furan, thiophene or pyrrole.

7. A process according to claim 5, wherein $R_1$ and $R_2$ as heteroaryl form a 5- or 6-membered ring having 1 or 2 identical or different hetero atoms.

8. A process according to claim 5, wherein $R_1$ and $R_2$ as heteroaryl-substituted alkyl are derived from a 5- or 6-membered ring having 1 or 2 identical or different hetero atoms.

9. A process according to claim 5, wherein $R_1$ and $R_2$ as heterocycloalkyl or as hetero-cycloalkyl-substituted alkyl contain from 4 to 6 ring atoms and 1 or 2 identical or different hetero atoms from the group O, S and $NR_6$, wherein $R_6$ is hydrogen, $C_1$–$C_{12}$alkyl, phenyl or benzyl.

10. A process according to claim 5, wherein $R_1$, $R_2$ and $R_3$ as alkyl are unsubstituted or substituted $C_1$–$C_6$alkyl.

11. A process according to claim 5, wherein $R_1$, $R_2$ and $R_3$ as unsubstituted or substituted cycloalkyl contain from 3 to 6 ring carbon atoms.

12. A process according to claim 5, wherein $R_1$, $R_2$ and $R_3$ as aryl are unsubstituted or substituted naphthyl or phenyl, and $R_1$, $R_2$ and $R_3$ as aralkyl are unsubstituted or substituted phenylalkyl having from 1 to 10 carbon atoms in the alkylene.

13. A process according to claim 5, wherein $R_1$ and $R_2$ together or $R_1$ and $R_3$ together form, with the carbon atom or with the -N=C group to which they are bonded, respectively, a 5- or 6-membered ring.

14. A process according to claim 5, wherein in formula I $R_3$ is 2,6-di-$C_1$–$C_4$alkylphen-1-yl, $R_1$ is $C_1$–$C_4$alkyl, and $R_2$ is $C_1$–$C_4$alkyl, $C_1$–$C_4$alkoxymethyl or $C_1$–$C_4$alkoxyethyl.

15. A process according to claim 14, wherein $R_3$ is 2,6-dimethylphen-1-yl or 2-methyl-6-ethylphen-1-yl, $R_1$ is ethyl or methyl, and $R_2$ is methoxymethyl.

16. A process according to claim 6, wherein the imine corresponds to formula

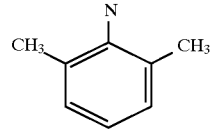 (Va)

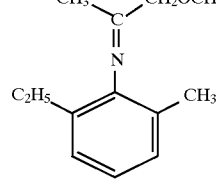 (Vb)

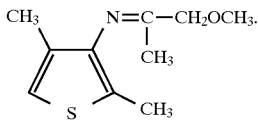

(Vc)

17. A process according to claim 1, wherein the iridium catalyst is a homogeneous catalyst that is substantially soluble in the reaction medium.

18. A process according to claim 1, wherein the catalyst corresponds to formula III, IIIa, IIIb, IIIc or IIId

[XIrYZ] (III),

[XIrY]$^{\oplus}$A$^{\ominus}$ (IIIa),

[YIrZ$_4$]$^{\ominus}$M$^{\oplus}$ (IIIb),

[YIrHZ$_2$]$_2$ (IIIc) or

[YIrZ$_3$]$_2$ (IIId), wherein X is two olefin ligands or a diene ligand, Y is a diphosphine having secondary phosphine groups (a) the phosphine groups of which are bonded to a carbon chain having from 2 to 4 carbon atoms, or (b) the phosphine groups of which are either bonded directly or via a bridge group —CR$_a$R$_b$- in the ortho positions of a cyclopentadienyl ring or are each bonded to a cyclopentadienyl ring of a ferrocenyl, or (c) one phosphine group of which is bonded to a carbon chain having 2 or 3 carbon atoms and the other phosphine group of which is bonded to an oxygen atom or a nitrogen atom bonded terminally to that carbon chain, or (d) the phosphine groups of which are bonded to the two oxygen atoms or nitrogen atoms bonded terminally to a C$_2$-carbon chain; with the result that in the cases of (a), (b), (c) and (d) a 5-, 6- or 7-membered ring is formed with the Ir atom, the radicals Z are each independently of the other(s) Cl, Br or I, A$^{\ominus}$ is the anion of an oxy or complex acid, and M$^{\oplus}$ is an alkali metal cation or quaternary ammonium, and R$_a$ and R$_b$ are each independently of the other hydrogen, C–C$_8$alkyl, C$_1$–C$_4$fluoroalkyl, phenyl or benzyl or are phenyl or benzyl having from one to three C$_1$–C$_4$alkyl or C$_1$–C$_4$alkoxy substituents.

19. A process according to claim 18, wherein the diphosphine Y contains at least one chiral group.

20. A process according to claim 18, wherein X as an olefin ligand is branched or linear C$_2$–C$_{12}$alkylene; and X as a diene ligand is an open-chain or cyclic diene having from 4 to 12 carbon atoms.

21. A process according to claim 18, wherein the secondary phosphine groups contain two identical or different radicals from the following group: linear or branched C$_1$–C$_{12}$alkyl; unsubstituted or C$_1$–C$_6$alkyl- or C$_1$–C$_6$alkoxy-substituted C$_5$–C$_{12}$cycloalkyl, C$_5$–C$_{12}$cyclo-alkyl-CH$_2$-, phenyl or benzyl; or phenyl or benzyl substituted by halogen (e.g. F, Cl or Br), C$_1$–C$_6$haloalkyl, (C$_1$–C$_{12}$alkyl)$_3$Si, (C$_6$H$_5$)$_3$Si, C$_1$–C$_6$haloalkoxy (e.g. trifluoromethoxy), -NH$_2$, phenyl$_2$N-, benzyl$_2$N-, morpholinyl, piperidinyl, pyrrolidinyl, (C$_1$–C$_{12}$alkyl)$_2$N-, -ammonium-X$_1$$^{\ominus}$, —SO$_3$M$_1$, —CO$_2$M$_1$, —PO$_3$M$_1$ or by —COO-C$_1$–C$_6$alkyl (e.g. —COOCH$_3$), wherein M$_1$ is an alkali metal or hydrogen and X$_1$$^{\ominus}$ is the anion of a monobasic acid.

22. A process according to claim 18, wherein the diphosphine Y is of the formula:

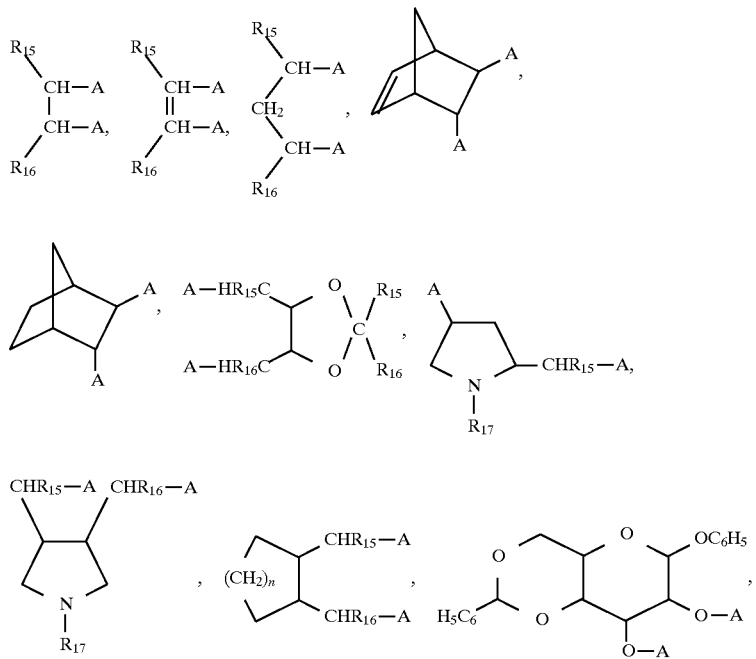

-continued

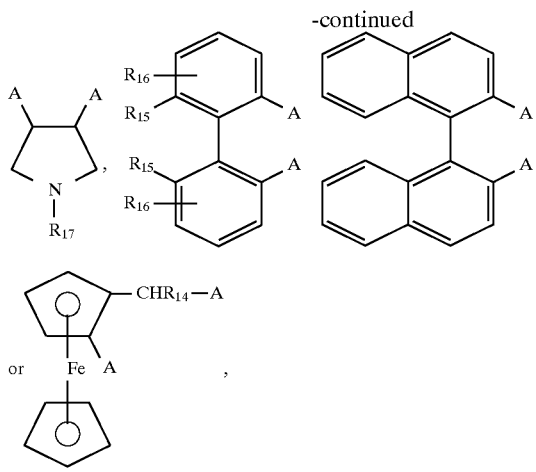

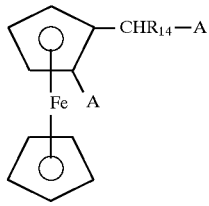

wherein
  $R_{15}$ and $R_{16}$ are each independently of the other hydrogen, C1–$C_4$alkyl, phenyl, benzyl, or phenyl or benzyl having from one to three $C_1$–$C_4$alkyl or $C_1$–$C_4$alkoxy substituents,
  $R_{14}$ is hydrogen, $C_1$–$C_4$alkyl, phenyl, benzyl, or phenyl or benzyl having from one to three $C_1$–$C_4$alkyl or $C_1$–$C_4$alkoxy substituents,
  $R_{17}$ is hydrogen, $C_1$–$C_4$alkyl, phenyl, benzyl, $C_1$–$C_6$alkoxy-CO-, $C_1$–$C_6$alkyl-CO-, phenyl-CO-, naphthyl-CO- or $C_1$–$C_4$alkylNH-CO-,
  A represents identical or different groups —P(R)$_2$, wherein R is C1–$C_6$alkyl, cyclohexyl, phenyl, benzyl, or phenyl or benzyl having from one to three $C_1$–$C_4$alkyl, disubstituted amino, $C_1$–$C_4$alkoxy, —CF$_3$ or partially or fully fluorinated $C_1$–$C_4$alkoxy substituents, and n is 0, 1 or 2.

23. A process according to claim 18, wherein the secondary phosphine groups of the diphosphines Y are bonded either directly or via a bridge group —CR$_a$R$_b$- in the ortho positions of a cyclopentadienyl ring or are each bonded to a cyclopentadienyl ring of a ferrocenyl.

24. A process according to claim 23, wherein the diphosphine corresponds to formula X $$\text{X}$$

wherein $R_{14}$ is hydrogen, $C_1$–$C_4$alkyl, phenyl, benzyl, or phenyl or benzyl substituted by from one to three $C_1$–$C_4$alkyl or $C_1$–$C_4$alkoxy substituents, A represents identical or different groups —P(R)$_2$ wherein R is $C_1$–$C_6$alkyl, cyclohexyl, phenyl, benzyl, or phenyl or benxyl substituted by from one to three $C_1$–$C_4$alkyl, disubstituted amino, $C_1$–$C_4$alkoxy, —CF$_3$, or partially or fully fluorinated $C_1$–$C_4$alkoxy substituents.

25. A process according to claim 24, wherein the diphosphine of formula X is chiral and $R_{14}$ is $C_1$–$C_4$alkyl, or is phenyl or benzyl substituted by from one to three $C_1$–$C_4$alkyl or $C_1$–$C_4$alkoxy substituents, A represents identical or different groups —P(R)$_2$ wherein R is $C_1$–$C_6$alkyl, cyclohexyl, phenyl, benzyl, or phenyl or benzyl substituted by from one to three $C_1$–$C_4$alkyl, disubstituted amino, $C_1$–$C_4$alkoxy, —CF$_3$ or partially or fully fluorinated $C_1$–$C_4$alkoxy substituents.

26. A process according to claim 18, wherein the diphosphine Y is
  {(R)-1-[(S)-2-diphenylphosphino)ferrocenyl]}ethyl-di(3,5-dimethyl-phenyl)phosphine,
  {(R)-1-[(S)-2-diphenylphosphino)ferrocenyl]}ethyl-di(3,5-dimethyl-4-N,N-dipropyl-aminophenyl)phosphine,
  {(R)-1-[(S)-2-diphenylphosphino)ferrocenyl]}ethyl-di(3,5-di-iso-propyl-4-N,N-dimethyl-aminophenyl)phosphine,
  {(R)-1-[(S)-2-diphenylphosphino)ferrocenyl]}ethyl-di(3,5-di-iso-propyl-4-N,N-di-benzylylaminophenyl)phosphine,
  {(R)-1-[(S)-2-diphenylphosphino)ferrocenyl]}ethyl-di(3,5-dimethyl4-N,N-dibenzylyl-aminophenyl)phosphine,
  {(R)-1-[(S)-2-diphenylphosphino)ferrocenyl]}ethyl-di(3,5-dimethyl4-(1'-pyrrolo)-phenyl)phosphine,
  {(R)-1-[(S)-2-diphenylphosphino)ferrocenyl]}ethyl-di(3,5-dimethyl4-N,N-dipentyl-aminophenyl)phosphine,
  {(R)-1-[(S)-2-diphenylphosphino)ferrocenyl]}ethyl-di(3,5-dimethyl4-N,N-dimethyl-aminophenyl)phosphine,
  1,4-bis(diphenylphosphino)butane or
  {(R)-1-[(S)-2-di(4-methoxyphenyl)phosphino)ferrocenyl]}ethyl-di(3,5-dimethyl4-N,N-dimethylaminophenyl)phosphine.

27. A process according to claim 1, wherein hydrogen iodide is used in the form of an aqueous solution.

28. A process according to claim 27, wherein hydrogen iodide is used in gaseous form.

29. A process according to claim 1, wherein the molar ratio of imine to iridium catalyst is from 5 000 000 to 10.

30. A process according to claim 29, wherein the molar ratio of imine to iridium catalyst is from 1 000 000 to 1000.

31. A process according to claim 1, wherein the molar ratio of imine to hydrogen iodide is from 1 000 000 to 100.

32. A process according to claim 31, wherein the molar ratio of imine to hydrogen iodide is from 10 0000 to 1000.

33. A process according to claim 1, wherein the reaction temperature is from −20° to 100° C.

34. A process according to claim 1, wherein the hydrogen pressure is from 5 to 150 bar.

35. A process according to claim 1, wherein the hydrogenation is carried out in a loop reactor.

36. A process according to claim 1, wherein an aldimine or a ketimine formed in situ before or during the hydrogenation is hydrogenated.

37. A process for the preparation of a compound of the formula

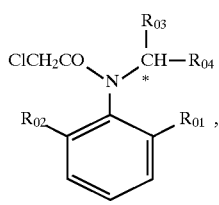 (IV)

wherein $R_{01}$, $R_{02}$ and $R_{03}$ are each independently of the other $C_1$–$C_4$alkyl, and $R_{04}$ is $C_1$–$C_4$alkyl or $C_1$–$C_4$alkoxymethyl or $C_1$–$C_4$alkoxyethyl, by (1) hydrogenation of an imine of the formula

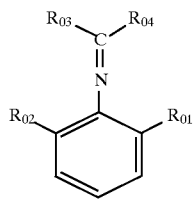 (V)

with hydrogen in the presence of an iridium catalyst and with or without an inert solvent to form an amine of the formula

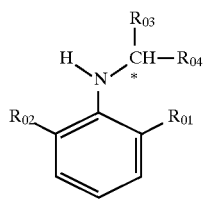 (VI)

and (2) reaction thereof with the compound of formula $ClCH_2CO—Cl$ (VII), wherein in the hydrogenation the reaction mixture contains hydrogen iodide.

38. A process according to claim 37, wherein the hydrogenation proceeds asymmetrically in the presence of asymmetric iridium catalysts.

39. A process according to claim 37, wherein the imine hydrogenated is a compound of the formula

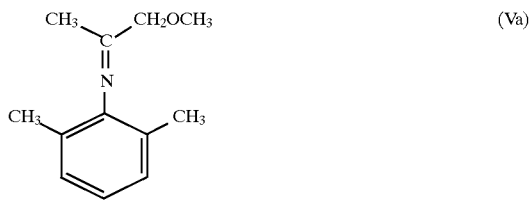 (Va)

or

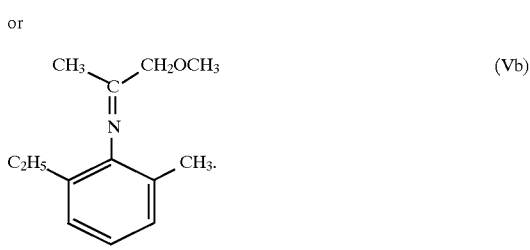 (Vb)

40. A process according to claim 39, wherein the compounds are hydrogenated asymmetrically in the presence of asymmetric iridium catalysts.

41. A process according to claim 40, wherein the hydrogenated compounds have the S-configuration at the asymmetric carbon atom.

* * * * *